United States Patent [19]

Lysaght et al.

[11] Patent Number: 4,842,576
[45] Date of Patent: Jun. 27, 1989

[54] SYSTEM FOR GENERATING SUBSTANTIALLY CONSTANT FLUID PRESSURE

[75] Inventors: Michael J. Lysaght, Barrington; Daniel R. Boggs; Philip L. Ritger, both of Vernon Hills, all of Ill.

[73] Assignee: Baxter International Inc., Deerfield, Ill.

[21] Appl. No.: 919,044

[22] Filed: Oct. 15, 1986

[51] Int. Cl.[4] .............................. A61M 37/00
[52] U.S. Cl. ........................ 604/6; 604/134; 604/131; 222/101
[58] Field of Search .................. 604/4, 7, 27–30, 604/73, 80–81, 131, 132, 150, 151, 153, 185, 182, 403, 407, 6, 134; 222/95, 99, 101–102

[56] References Cited

U.S. PATENT DOCUMENTS

| Re. 32,089 | 3/1986 | Blatt et al. . |
| 2,502,081 | 3/1950 | Flynn et al. . |
| 3,151,616 | 10/1984 | Selfon . |
| 3,198,385 | 8/1985 | Maxwell . |
| 3,543,966 | 12/1970 | Ryan .................. 222/101 |
| 3,647,117 | 3/1972 | Hargest . |
| 3,655,123 | 4/1972 | Judson et al. . |
| 3,670,926 | 6/1972 | Hill . |
| 3,895,741 | 7/1975 | Nugent . |
| 4,027,784 | 6/1977 | Mattson ............... 222/102 |
| 4,044,764 | 8/1977 | Szabo et al. .......... 604/134 |
| 4,191,182 | 3/1980 | Popovich et al. . |
| 4,212,742 | 7/1980 | Solomon et al. . |
| 4,237,881 | 12/1980 | Beigier et al. . |
| 4,284,502 | 8/1981 | Kramer . |
| 4,381,775 | 5/1983 | Nose' et al. . |
| 4,430,078 | 2/1984 | Sprague . |
| 4,447,191 | 5/1984 | Bilstad et al. . |
| 4,458,539 | 7/1984 | Bilstad et al. . |
| 4,479,760 | 10/1984 | Bistad et al. . |
| 4,479,761 | 10/1984 | Bilstad et al. . |
| 4,479,762 | 10/1984 | Bilstad et al. . |
| 4,481,827 | 11/1984 | Bilstad et al. . |
| 4,493,693 | 1/1985 | Bilstad et al. . |
| 4,498,983 | 2/1985 | Bilstad et al. . |
| 4,526,515 | 7/1985 | DeVries . |
| 4,551,136 | 11/1985 | Mandl . |
| 4,551,139 | 11/1985 | Plass et al. . |
| 4,557,728 | 12/1985 | Sealfon et al. . |
| 4,573,962 | 3/1986 | Troutner . |
| 4,588,407 | 5/1986 | Isono et al. . |
| 4,605,503 | 8/1986 | Bilstad et al. . |
| 4,614,513 | 9/1986 | Bensinger . |

FOREIGN PATENT DOCUMENTS

| 0175618 | 3/1984 | European Pat. Off. . |
| 0114698 | 8/1984 | European Pat. Off. . |
| 8400114 | 8/1984 | Netherlands ............. 604/131 |
| 2118634 | 11/1983 | United Kingdom ....... 604/131 |

Primary Examiner—C. Fred Rosenbaum
Assistant Examiner—Kathleen A. Daley
Attorney, Agent, or Firm—Paul C. Flattery; Bradford R. L. Price; Daniel D. Ryan

[57] ABSTRACT

A system for generating substantially constant fluid pressure is provided for forcing fluid from a variable volume container. The system includes a roller that rotates in response to a constant applied torque to force fluid from the flexible container under a substantially constant pressure. Two spaced apart parallel rollers can exert force on both sides of the container.

22 Claims, 9 Drawing Sheets

39cm S.I. Tbg WACO78170-10
Silicone Tubing engaged after
fall of 15cm

3/4" rollers m = 481 Kg
Wheel dia. = 2 1/4"
needle = 18ga.

SYSTEM FOR GENERATING SUBSTANTIALLY CONSTANT FLUID PRESSURE

TECHNICAL FIELD

The invention generally pertains to the field of fluid pumping systems. More particularly, the invention pertains to fluid pumping systems which employ pressure generating devices and methods to transport fluids.

The invention also pertains to the processing of blood components using lightweight pumping equipment capable of easy transport.

BACKGROUND OF THE INVENTION

The development of single needle, disposable blood collection systems has provided a safe, relatively inexpensive and accepted modality for collecting units of whole blood from volunteer donors. Such units of whole blood are usually centrifugally separated into various therapeutic components, such as red blood cells, platelets, and plasma, for transfusion. Such systems have made possible large-scale collection of whole blood from volunteer donors at sites such as church halls, schools or offices remote from medical facilities. The availability whole blood collection systems suitable for volunteer donors is important, because it provides access to a relatively large pool of healthy individuals from which to draw needed supplies of whole blood components for life-saving or therapeutic purposes.

The conventional whole blood collection systems, familiar to and accepted by volunteer donors, can be used to collect plasma, as just described. However, such systems, by design, yield only a single unit of plasma per donor. Furthermore, such systems, by design, also take red blood cells from the donor. The donor must internally replace red blood cells before he or she can donate again. This replacement process takes six to twelve weeks, during which time the donor cannot give blood. Thus, such conventional whole blood collection systems are not suited for collecting the relatively large pools of plasma (called "source plasma") from which the various therapeutic plasma proteins, such as albumin and AHF (anti-hemophilic factor) are obtained by fractionation.

Therefore, the collection of source plasma from volunteer donors, as opposed to the collection of whole blood, is not widespread. As a result, much of the source plasma now collected comes from paid donors, not volunteer donors. It would be desirable to make the collection of source plasma a volunteer-based activity to a much greater extent than it is currently.

Various methods are known for the collection of source plasma (also called plasmapheresis). For example, using a modification of the above-described whole blood collection system, a unit of whole blood is collected and separated by centrifugation into red blood cells and plasma. The plasma is retained, while the red blood cells are immediately returned to the donor. The process is then repeated, collecting another unit of plasma and returning another unit of red blood cells. The result is the collection of two units of plasma for fractionation purposes. Because red blood cells are returned to the donor, this process allows more frequent donation, often as frequently as once per week. However, this process is time-consuming and, in part for this reason, does not appeal to volunteer donors. Furthermore, during the process, while the whole blood is being separated into red blood cells and plasma, the blood collection system (typically a series of integrally attached bags) is physically separated from the donor. Such physical separation requires procedures to minimize the risk of error when several donors are being processed simultaneously that one donor's red blood cells are not inadvertently returned to another donor. In addition, physical separation of the blood from the donor potentially raise concerns in the collection staff of exposure to infectious agents in the collected blood if fluid drips or leaks occur.

On-line extracorporeal separation systems, in which the blood collection system is not physically separated from the donor during the collection procedure, are also known. These can be either batch or continuous systems. Such systems employ either centrifugal separators or membrane filters.

A centrifuge-based system is disclosed in Judson et al. U.S. Pat. No. 3,655,123 entitled "Continuous Flow Blood Separator." The system of the Judson et al. patent was two needles, an outflow needle and a inflow needle. Whole blood is drawn from a donor via the outflow needle. The whole blood fills a buffer bag. Blood from the buffer bag drains, under the force of gravity into a centrifuge. The system of the Judson et al. patent uses the centrifuge to separate blood components. The plasma can be collected in a container. The red blood cells can be returned to the donor via the inflow needle.

A membrane-based system is disclosed in Popovich et al., U.S. Pat. No. 4,191,182.

The systems of the Judson et al. and Popovich et al. patents require an external source of electrical energy. Further, the systems rely upon a variety of mechanical components, including pumps and the centrifuge that prevent it from being readily portable.

Systems that include pumps are often constant volume systems, in which a relatively constant volume of fluid is pumped through the system per unit of time. Constant volume pumping systems suffer from the disadvantage that sudden over pressure conditions can occur if one of the fluid flow lines becomes crimped or is partly closed. These over pressure conditions are particularly undesirable in on-line extracorporeal blood separation systems, in which the fluid system of the blood separation device is in flow communication with the donor's blood circulation system.

The known extracorporeal separation systems therefore tend to be expensive, complex, not always "donor friendly", and generally unsuited for portable operation.

One system of membrane collection suitable for portable operation has been described in a published European Patent Application, Publication No. 0114698 published Aug. 1, 1984; entitled "Process and Apparatus for Obtaining Blood Plasma." In this system, a unit of blood is withdrawn from a donor into a set containing a membrane filter, tubing and a sterile blood receptacle. The whole blood is first passed through the filter. The plasma flows through the membrane filter and is collected in a separate plasma container. The remainder of the blood unit, which had passed from the inlet to the outlet of the filter, is accumulated in the sterile container such as a standard blood bag. It can then be immediately returned to the donor.

In this approach, the pressure available for driving the filtration process and for propelling the blood from the inlet to the outlet of the filter is relatively small. This pressure includes the donor's venous pressure (with an inflatable cuff, being on the order of 40 mm Hg) and available hydrostatic head (approximately 50 mm Hg) for a total pressure on the order of 90 mm Hg. These pressures may vary from donor to donor and from site to site. This can result in a relatively slow and variable plasma collection time. It also requires relatively large filters to function at the available low driving pressures. It can also be difficult to achieve precise anticoagulant flow proportional to blood flow with inexpensive and simple-to-use hardware.

Another membrane-based system is disclosed in a group of three U.S. Pat. No. 4,479,760 entitled "Actuator Apparatus for a Prepackaged Fluid Processing Module Having Pump and Valve Elements Operable in Response to Applied Pressures"; U.S. Pat. No. 4,479,761 entitled "Actuator Apparatus for a Prepackaged Fluid Processing Module Having Pump and Valve Elements Operable in Response to Externally Applied Pressures"; and U.S. Pat. No. 4,479,762 entitled "Prepackaged Fluid Processing Module Having Pump and Valve Elements Operable in Response to Applied Pressures," all issued to Bilstad et al. The system of the Bilstad et al. patents utilizes a disposable module containing a hollow membrane filter, a plasma container and other elements. A fixture is provided to receive the module during the donation cycle. Constant volume pumps in the fixture are provided to draw whole blood from the donor into the inlet side of the filter and to return the concentrated red cells to the donor from the outlet side of the filter. A single needle is used from both drawing the whole blood from the donor and returning concentrated red blood cells to the donor.

The system of the Bilstad et al. patents requires an exterior source of electrical energy. In addition, the fixtures can be relatively expensive and complex.

Thus there still continues to be a need for pumping systems providing substantially more pressure than gravity-fed systems, but without the potential of undesirable over pressure conditions. Such improved pumping systems would find particular application in the field of blood component collection, especially if such systems were also simple to operate and capable of easy transport.

SUMMARY OF THE INVENTION

The invention provides pumping systems which offer both efficiency and simplicity of operation. In accordance with the invention, instead of using gravity or constant volume pumping devices, pumping systems which generate substantially constant fluid pressures are provided.

In one embodiment, the pumping system which incorporates the features of the invention is employed to express fluid from a variable volume container and into a separator at a substantially constant pressure. In the separator, the fluid is separated into component parts.

This system is particularly well suited for the collection of plasma using a membrane filtration device as the separator. The use of substantially constant pressure lends itself to optimization of the filtration technique.

By virtue of the invention, substantialy pressures can be generated without having to raise the fluid container to inconvenient heights. In addition, the constant pressure provided by the invention does not increase substantially should an obstruction occur in the flow path.

In its preferred embodiment, the desired substantially constant pressure is achieved by an apparatus having spaced-apart rollers between which a flexible fluid container is passed, thereby expressing its contents. The rollers are rotated in response to constant, applied force. This force can be generated by a hanging weight. Alternately, a constant-force spring can be used. An essentially constant torque is applied to the rollers.

Other features and advantages of the present invention will become readily apparent from the following detailed description, the accompanying drawings, and the appended claims.

DETAILED DESCRIPTION OF THE PREFERRED EMBODIMENT

The present invention is susceptible of diverse embodiments. Several alternate embodiments are shown and described. However, it should be understood that the present disclosure is to be considered as an exemplification of the invention, and is not intended to limit the invention to the specific embodiments illustrated.

Figure 1:
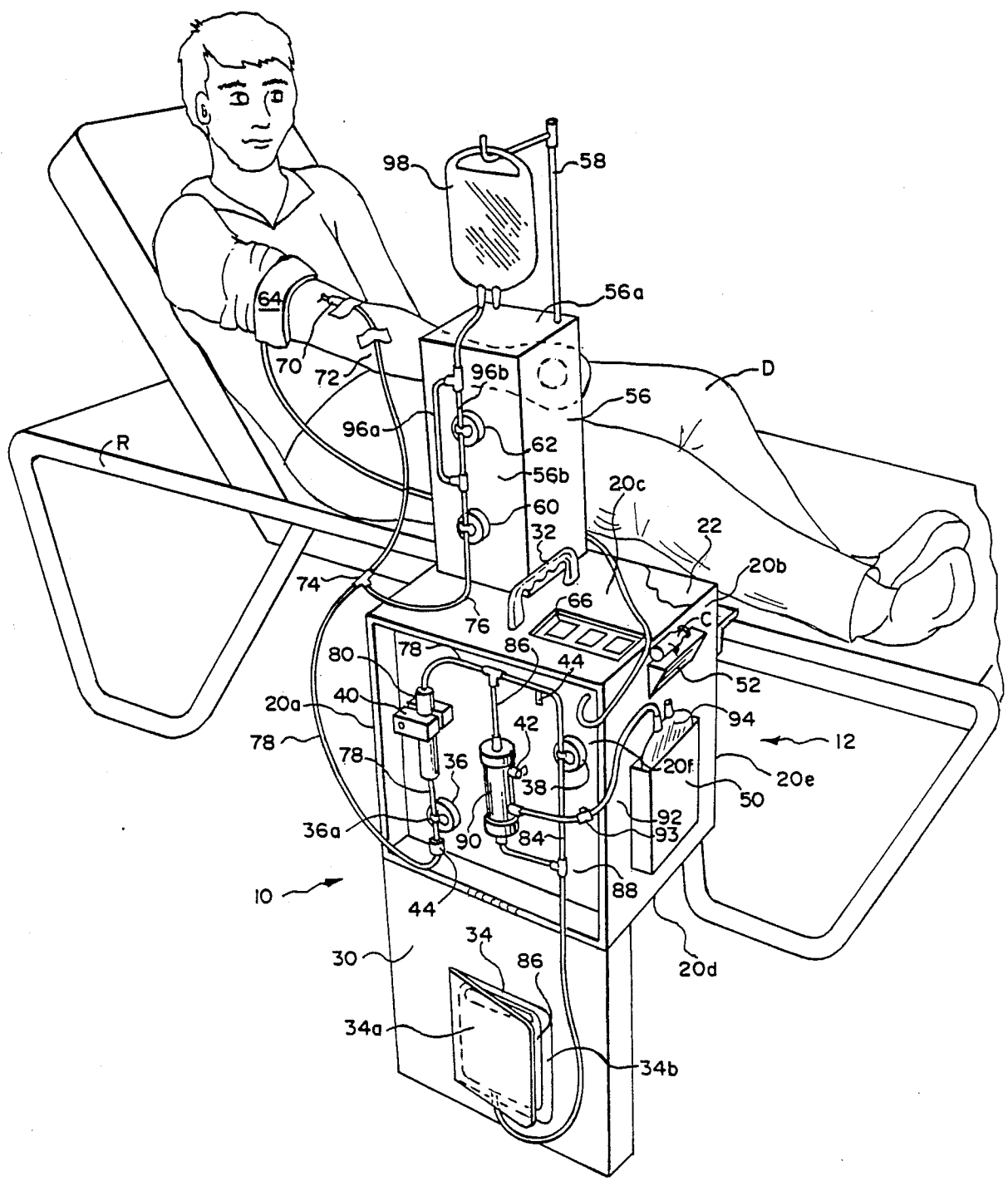
FIG. 1 is a pespective view of a plasmapheresis system, configured for use, in accordance with the present invention.
Figure 2:
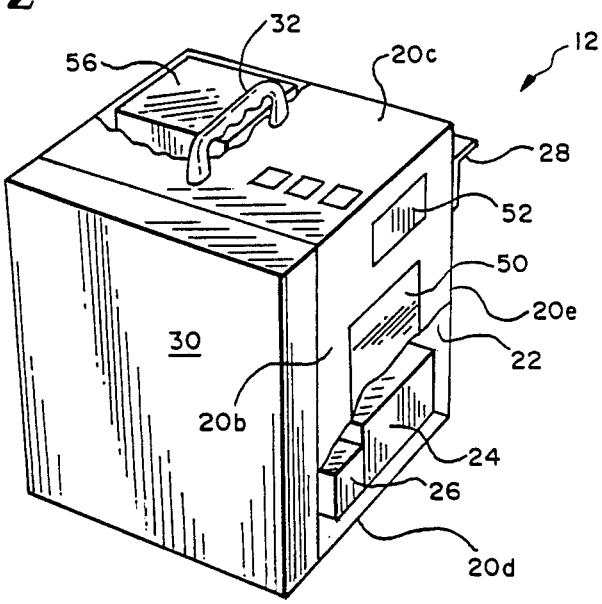
FIG. 2 is a perspective view, partly broken away of a fixture, configured for transportation, in accordance with the present invention.
Figure 3:
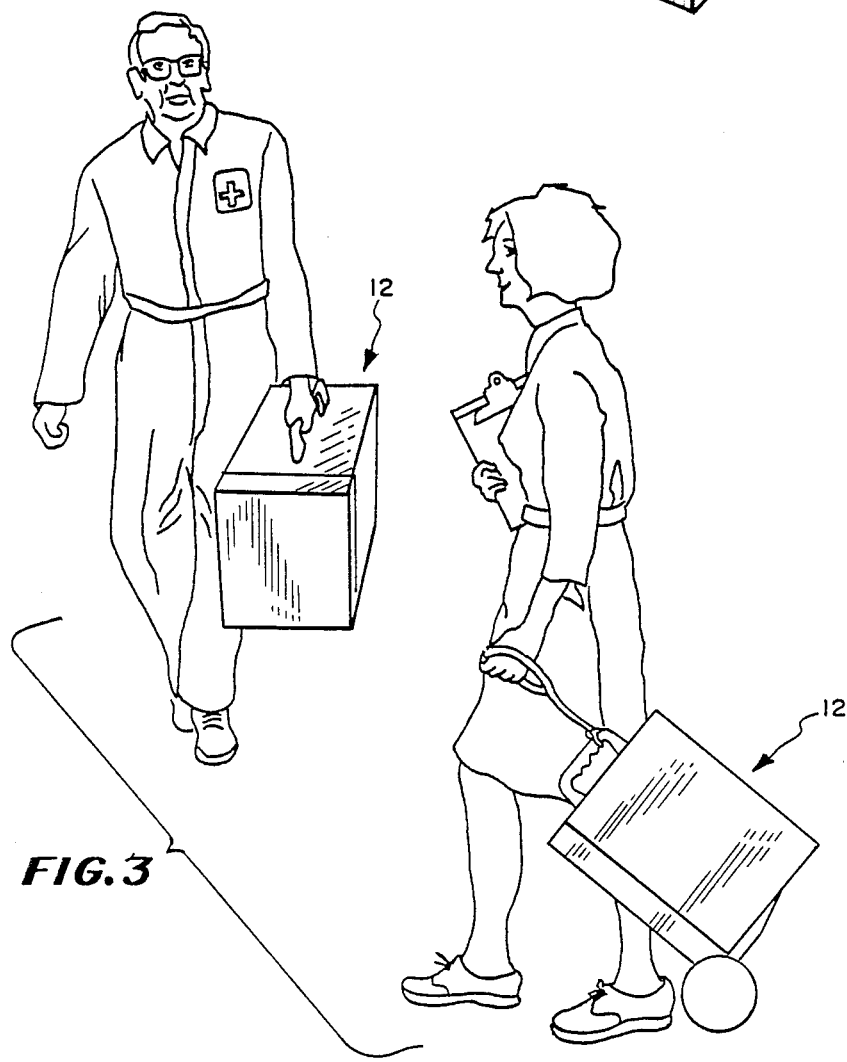
FIG. 3 is a pictorial view illustrating portability of the fixture in FIG. 2.

A self-contained, portable system 10 usable for the collection of blood components from donors is illustrated in FIGS. 1 to 3. In the particular embodiment, the system 10 is intended to collect plasma from volunteer donors. In this embodiment, the system 10 includes a portable, self-contained and reusable fixture 12. The system 10 also includes a single-use, disposable, integrally-formed collection set 14. The set 14 is mounted in the fixture 12 during the collection process.

The fixture 12 includes a housing 20 which can be formed of a metal or plastic. The housing 20 has sides 20a, 20b; a top and bottom 20c, 20d and rear surface 20e. Housing 20 defines or forms a closed interior region 22 in which is located a control unit 24 (see FIG. 2).

Affixed to the rear surface 20e is a pair of clamps 28. The clamps 28 are intended to engage a rail R of a blood donation cot or bed, as shown in FIG. 1. Such cots are currently regularly used in connection with the collection of whole blood from volunteer donors.

The clamps 28 support the fixture 12 at an appropriate working height without any need for supporting legs or tables. The clamps 28 fold that against the rear surface 20e for storage and transportation.

The housing 20 has a hinged front cover 30. During transportation, the cover 30 is closed and latched. The overall size of the fixture 12 when closed for the transportation and storage is on the order of 12" wide by 12" deep by 14" high. A handle 32 is attached to the top surface 20c for use during transportation.

The hinged cover 30 supports, below the donor D, a whole blood collection container support or receptacle 34 with a hinged cover 34a. Located in the blood container support 34 is a force applying system 34b.

The fixture 12 also includes an energy source 51 for the force applying system 34b, as well as for the control system 24. The source 51 is self-contained in the housing 20, so that operation of the fixture 12 is independent of any external source of energy.

A recessed front panel 20f on the housing 20 supports pneumatically operated clamps 36 and 38, a bubble sensor 40, a plasma separator support clamp 42 and tubing supports 44. The clamps 36, 38 are of a type conventionally used to close off flexible tubing members. In an unenergized condition, a spring biased clamping bar, such as the bar 36a, pinches the tubing in the clamp closed. When energized, by fluid pressure, the clamping bar moves away from the tubing member permitting fluid to flow. The bubble sensor 40 is an ultrasonic sensor of a type conventionally used with blood donation and return systems to sense a gas-liquid interface. The sensor 40 is powered by a battery 26 housed within the interior region 22 (see FIG. 2).

Support 42 could be a spring clamp capable of removably supporting a cylindrical plasma separator such as a filter. Tubing supports 44 can correspond to small, L-shaped hangers of a type used to temporarily support flexible tubing.

Slidably affixed to the side 20b is a plasma container support 50. The support 50 can be a three-sided housing with a bottom but no top. Part of the side 20b forms the fourth side of the support 50. When the fixture 12 is being transported, the support 50 is pushed flat against the side 20b, as shown in FIG. 2.

While the energy source 51 can be variously constructed, in the embodiment shown in FIGS. 1 to 5, the source 51 includes a hinged cover and receiver 52. The receiver 52 can be opened to receive a module containing a releasable charge of energy. In the illustrated embodiment, the module takes the form of a $CO_2$ cartridge C inserted in the fixture 12 to provide a modular, self-contained fluidic, charge of energy to actuate the fluidic control system 24, the force applying system 34b, as well as the clamps 36, 38, 60 and 62. Alternately, the module can take the form of a battery, either single use or rechargeable.

A pop-up column 56 extends from the top 20c. The column 56 supports an L-shaped, tubular, anticoagulant support member 58 at a top surface 56a. The L-shaped support member 58 provides a hanger, located above the blood collection-support member 34 for a bag or container of anticoagulant solution. The pop-up column 56, on a front surface 56b supports two additional tubing clamps 60 and 62. The clamps 60, 62, as is discussed subsequently, are used to regulate the flow of anticoagulant when the system 10 is in use. For storage or transportation, the tubular support member 58 is retractable into the column 56. The column 56 is in turn pushed downward into the region 22. The top surface 56a then is positioned adjacent the top 20c of the fixture 12.

An inflatable cuff 64 is provided, coupled to the control unit and timer 24. A control panel 66 with a plurality of push buttons is positioned on the surface 20c.

FIG. 2 illustrates the fixture 12 with the cover 30 closed and the column 56 retained for storage and transportation. The fluidic control unit 24 and the battery 26 are also illustrated in FIG. 2 positioned in the interior region 22. The hangers 28 can be closed flat against the surface 20e during transportation.

FIG. 3 illustrates the portability of the fixture 12 when it is being taken to donation sites. The fixture 12 can be easily carried or pulled on a small cart of the type used to transport luggage. When the fixture 12 arrives at the donation site, it is mounted on the side of an available donor bed, as illustrated in FIG. 1 and opened. The set 14 can be mounted in the fixture 12. The modular $CO_2$ cartridge C can be inserted in the receiver 52, and used to energize the fixture 12. No additional external source of energy is needed to actuate the control system 24, the force applying system 34b, and the clamps 36, 38, 60, and 62 of the fixture 12 to carry out the donation process. Provision can be made in the fixture 12 for a storage region in which additional cartridges can be kept prior to use.

As an alternate to the column 56, the housing 20 can be elongated and the clamps 60, 62 can be mounted on the recessed surface 20f, above the tubing member 78. In this embodiment, the clamps 60, 62 would be spaced apart horizontally from one another.

As an alternate to the clamps 28, the fixture 12 can be fitted with a pair of foldable rear legs. In this embodiment, the foldable front cover 30, when opened, can function as a front support. The fixture 12 in this embodiment will be self-supporting and will stand on the floor beside the donor bed.

Figure 4:
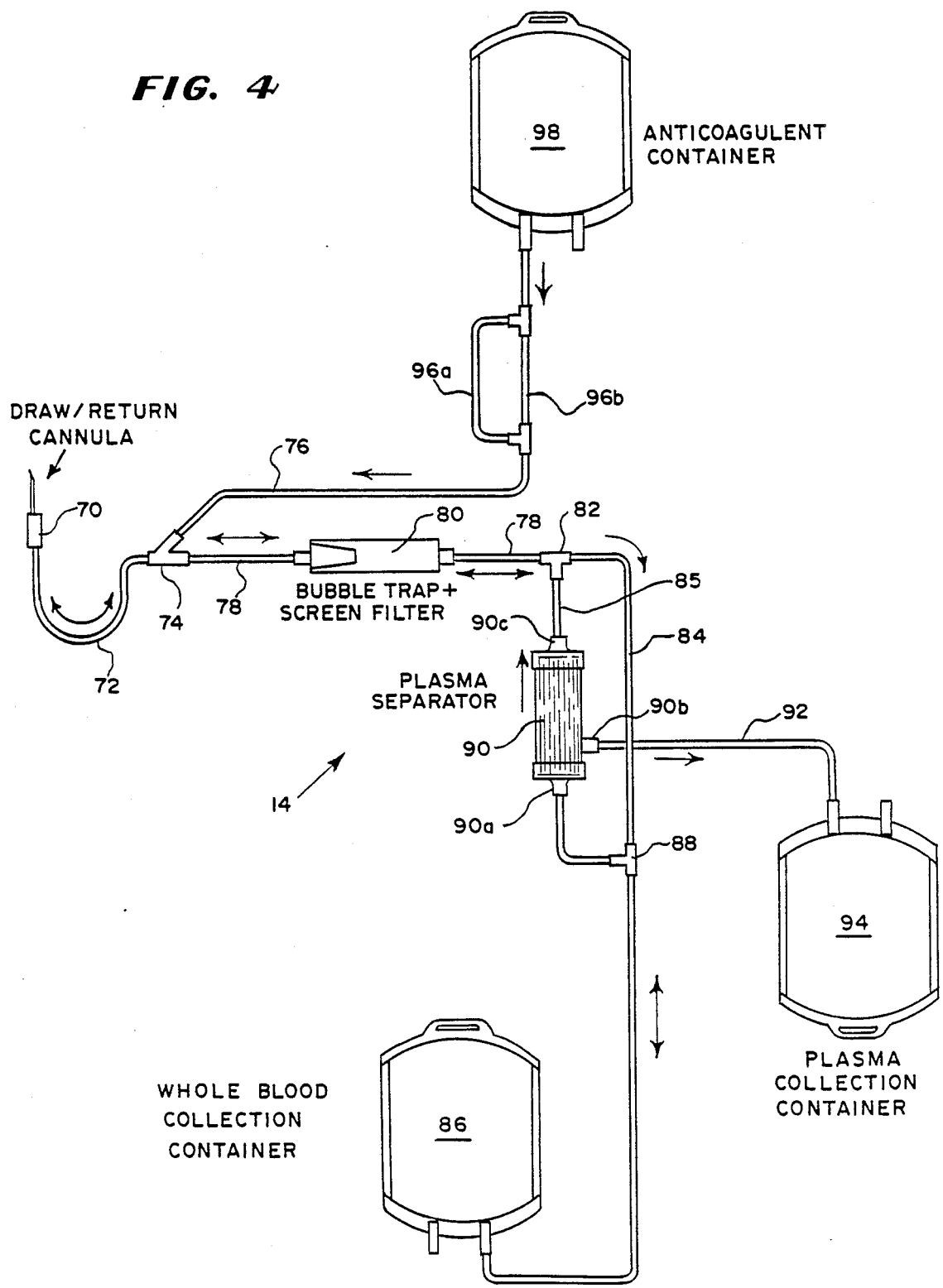
FIG. 4 is a planar view of a blood contacting set in accordance with the present invention.

FIG. 4 illustrates detail of the set 14. The set 14 includes a single lumen drawn/return cannula or phlebotomy needle 70. The cannula 70 has pointed end that can be inserted into a vein of a donor D, to provide access to the donor's whole blood.

The cannula 70 is coupled to a flexible fluid flow conduit or tubular member 72. The member 72 is coupled to a Y-shaped junction 74. The junction 74 is in turn coupled to an anticoagulant delivering tubular member 76 and a tubular member 78. The member 78 alternately receives whole blood from the cannula 70 and returns concentrated red blood cells to the donor D.

A combined bubble trap and screen filter unit 80 is located in the line 78. The unit 80 is conventional device manufactured by Travenol Laboratories, Inc.

A T-shaped coupling member 82 couples the tubing member 78 to tubing members 84 and 85. Tubing member 84 is in fluid flow communication with a whole blood collection container 86. The container 86 is preferably a variable volume container, meaning that the interior volume of the container expands to accommodate the introduction of fluid and can be contracted to reduce the interior volume so as to expel or displace the fluid contents. The variable volume container 86 can correspond to a flexible, conventional, blood collection bag. It can also correspond to a rigid or semirigid container which includes a collapsible portion to reduce its interior volume.

A T-shaped coupling member 88 is located in the line 84. The member 88 also places the collection bag 86 into fluid flow communication with an inlet 90a of a blood component separator 90, which, in the illustrated embodiment, separates plasma from the other components of whole blood, notably red blood cells and platelets. The plasma separator 90 can be implemented in a variety of ways. For example, and without limitation, the separator 90 could be implemented as a chromatography column, an electrophoretic apparatus or a membrane filter. The filter could incorporate planar membrane sheets, or cylindrical membrane fibers, and can also include a means for rotating the filter to enhance its filtration efficiencies. In a preferred form of the invention, the plasma separator is implemented as an optimized, hollow fiber membrane filter.

Coupled to and in fluid flow communication with a plasma output port 90b, via a flexible tubular member 92 is a plasma collection container 94. The container 94 could be a flexible plastic container similar to the container 86. An outlet 90c of the separator 90 is coupled to the tubular member 85.

The anticoagulant delivery member 76 is coupled via tubular members 96a and 96b to a container 98 of anticoagulant solution. The member 96a has a smaller internal diameter than does the member 96b. By means of these two flow paths, the anticoagulant can be easily and cheaply metered into the blood being collected via the tubing member 78. The arrows on FIG. 4 indicate directions of fluid flow when the set 14 is used with the fixture 12.

The tubing members of the set 14 can be formed of conventional, flexible plastic of a type suitable for contacting blood. The containers can be formed of conventional plastic now used in blood collection sets. Preferably, the set 14 comprises a sterile, integrally connected unit.

Figure 5:
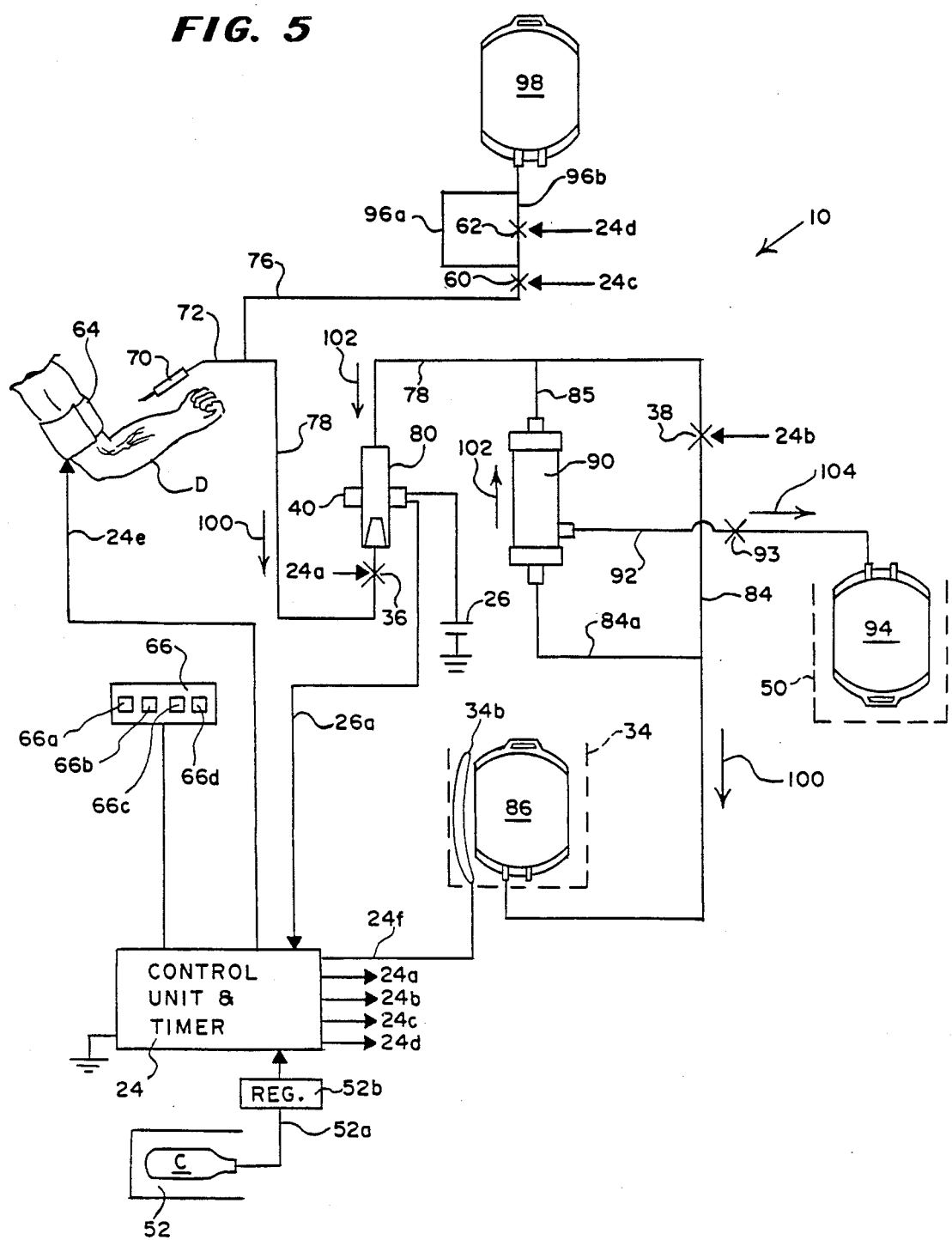
FIG. 5 is a schematic diagram of an apparatus and method for plasmapheresis in accordance with the present invention.

FIG. 5 illustrates the system 10 schematically. The fluidic control unit and timer 24 are coupled to the fluidic source of energy C via a fluid flow input line 52a and a regulator 52b. The control unit and timer 24 are also coupled via a plurality of fluid flow lines 24a, 24b, 24c and 24d the the fluidicly actuatable clamps 36, 38, 60 and 62, respectively. The unit 24 can selectively open each of the clamps 36, 38, 60 and 62 by providing fluidic energy on the respective line 24a, 24b, 24c and 24d. Fluidic line 24e couples the unit 24 to the inflatable cuff 64.

The bladder 34b can be inflated and deflated by the unit 24 via a fluidic control line 24f. The control unit and timer 24 receive electrical signals on the line 26a from the battery powered bubble detector 40. If the electrical signal on the line 26a indicates that a bubble has been detected in the line 78 during a return cycle, as discussed subsequently, the control unit 24 will permit clamp 36 to close thereby blocking any further flow in the line 78 to the donor D. An alarm condition can also be indicated on the panel 66.

The control unit and timer 24 can be implemented of standard fluidic logic components in accordance with the donor and return cycle described herein. The electrical signal on the line 26a can be coupled to a solenoid valve in the unit 24.

FIG. 5 illustrates use of the mobile plasma collection system 10 in accordance with the present invention. The donor D is positioned adjacent the sterile, sealed collection system 10. The system 10 includes the set 14 with the cannula 70, which could be a conventional, sterile single lumen phlebotomy needle of a type used in connection with blood collection. The needle 70 is coupled via flexible tubing 72, 78 and 84 of a conventional variety to the whole blood collection container or bag 86.

The collection bag 86 could be a flexible 500 ml plastic bag of a type now used for blood collection. The fluidicly operable clamp or valve 38 can be used to close off tubing member 84 under control of the unit 24. Closing the value 38 isolates the donor D from direct fluid flow communication from the container 86. Arrow 100 indicates the direction of flow of collected blood from the donor D into the collection bag 86. The whole blood drains from the donor D into the container or bag 86, as a result of the donor's internal blood pressure, which can be elevated in the region of the needle 70 by inflating the pressure cuff 64, as well as the force of gravity.

The container 86 is filled from the bottom as illustrated in FIGS. 1 and 5. Fill time with a normal donor will be in a range of 4-7 minutes. The draw rate with an average donor will be in a range of 70-100 ml/minute.

Anticoagulant solution is metered from the container 98 through the two-part conduit 96a, 96b of known resistance. The anticoagulant solution is metered into the blood simultaneously with the whole blood being collected from the donor D.

The two tubes 96a and 96b each have a selected diameter and length. The tube 96a has a smaller diameter than does the tube 96b. By having both tubes 96a and 96b open simultaneously for a selected period of time and then closing one tube off while the other remains open, the rate of flow and quantity of anticoagulant mixed with the blood flowing through the member 72 can be regulated. Valve 62 can be used to close off the larger diameter conduit 96b under control of the unit 24. The dual tube system with members 96a, 96b makes it possible to keep the level of anticoagulant in the blood in the lumens of the tubing members, such as the member 78, and in the collection bag 86 between predetermined upper and lower limits even though donor blood rate is variable.

When the donor D has provided a unit of whole blood, the valves 60 and 38 are closed, and the inflatable cuff 64 is deflated. A force applying system 34b is then activated by the control unit 24. While the force applying unit can be variously constructed, in the illustrated embodiment, the force applying system takes the form of an inflatable bladder, is illustrated in FIG. 5. The force applying system 34b can alternately be of a type that is mechanically or electrically activated, in which case the energy source 51 could take the form of a battery.

The generator 34b applies a force to the variable volume collection bag 86 to reduce its volume. The whole blood accumulated in the collection bag 86 is thus expressed or forced, through a conduit 84a into the plasma separator 90. The separator 90 will separate out 40–70% of the plasma in the whole blood passed through.

The whole blood passes through the separator 90 due to the force generator 34b in the direction 102. The plasma accumulates at the output port 90b and travels via the flexible tubing or conduit 92 to the plasma collection container 94. An arrow 104 indicates the direction of flow of the plasma.

The concentrated red blood cells, or residual blood component, exit from the separator 90 via the conduit 85, enter the conduit 78 and pass through the bubble trap and screen filter 80. The control unit 24 continuously monitors the electrical signal line 26a. In the event a bubble is detected in the trap 80, the clamp 36 is deenergized. Clamp 36, due to its internal spring biasing, immediately closes and blocks further fluid flow in the line 78 toward the donor D. An alarm condition can be indicated on the panel 66 and the operator can take corrective action.

If no bubbles are detected, the concentrated red blood cells will be simultaneously returned to the donor D via the line 78 and the same single-lumen cannula 70 used for whole blood collection. During the collection phase and the separation/return phase, the donor D is continuously coupled to the system 10 by means of the single-lumen cannula 70 and the bi-directional fluid-flow conduit 72, 78.

Due to the features of the invention, the whole blood passes through the separator 90 for separation, and the red blood cells are returned to the donor solely in response to the force applied to the bag 86 by the generator 34b, and without the application of any additional external force.

When the whole blood collection bag 86 has been emptied, a four to seven minute process, the plasma has been collected in the bag 94, and the remaining concentrated red blood cells have been returned to the donor D. The valves 38, 60, 62 can then be opened and the process repeated. The return rate of concentrated red blood cells is in a range of 40–80 ml/minute. Because the bag 86 is filled and drained from the bottom, all whole blood is expressed from the container. Depending on the rate of collection of plasma in the bag 94 the process may be repeated two or three times.

The relatively low cost of the interconnected set 14 is an advantage of the system 10. The interconnected plastic members can be used in the collection of plasma from a single user and then thrown away. In addition, since the bag 86 containing the collected blood remains continuously connected to the donor D, there is no chance that a donor D will accidentally receive the blood of another donor. Further, because the system 10 is continuously coupled to the donor D, the possibility of contamination is minimized.

The container 86 can be prefilled with sterile saline. The saline can be flushed from the container and the system 10 prior to the initiation of the initial blood collection cycle. Flushing or priming with saline insures a gas free system.

Figure 6:
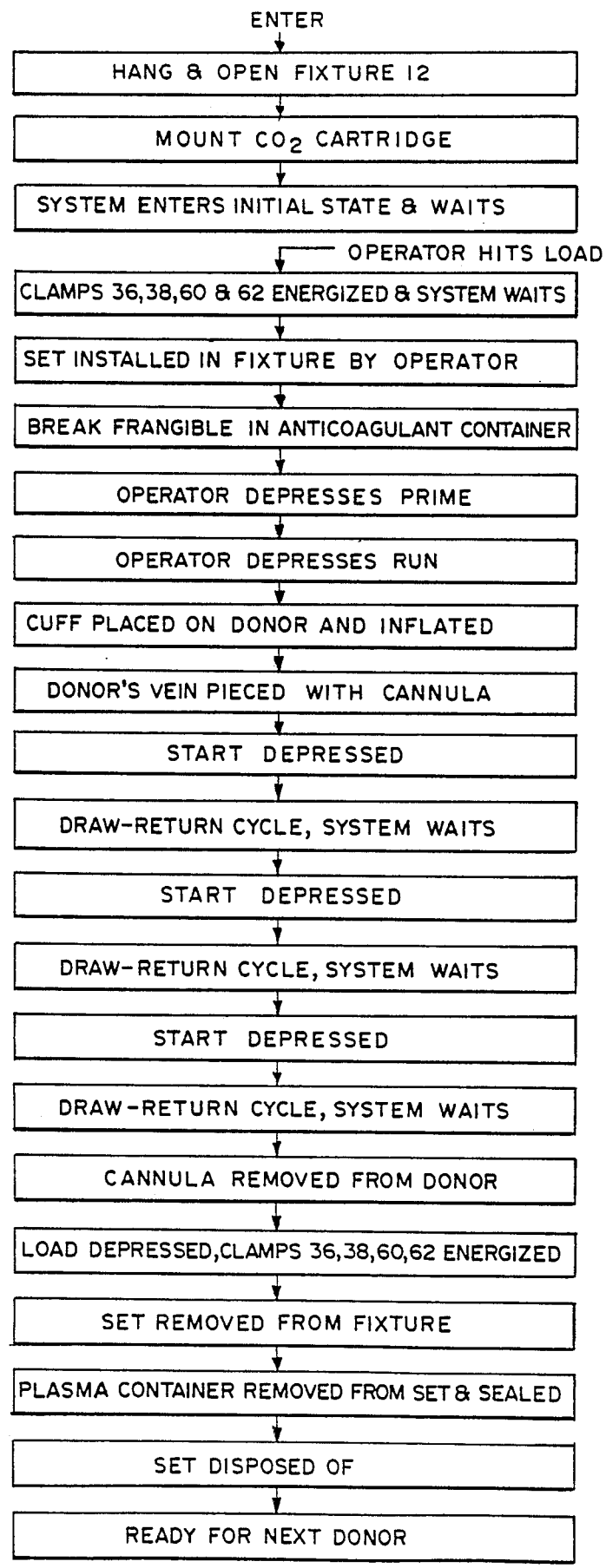
FIG. 6 is a flow diagram illustrating a method for plasmapheresis in accordance with the present invention.

An overall operational sequence is illustrated in the flow diagram of FIG. 6. The fixture 12 is hung on the donor bed the the cover 30 opened. A $CO_2$ cartridge C is removed from storage in the fixture 12 and inserted into the receptacle 52. This energizes the control unit and timer 24 which enters an initial state. When the operator is ready, the LOAD button 66a can be depressed. Upon sensing depression of the LOAD button 66a, the unit 24 energizes all clamps 36, 38, 60 and 64. The operator then installs the set 14 in the fixture 12.

The operator can then break a frangible seal in the anticoagulant container 98 permitting a fluid flow to fill the line 76. The operator then depresses the PRIME button 66b. Clamps 38, 60 and 62 close. The unit 24 then energizes the bladder 34b, via the line 24f to force saline through the line 84a, the separator 90 and the lines 85 and 78. A manually operated clamp 93 is closed by the operation to prevent fluid flow in line 92. After the separator 90 has been filled with saline, clamp 38 is energized to open the line 84 to the flow of saline. When the entire set 14 has been flushed and saline has run out of the cannula 70 the operator depresses the RUN button 66c. The system 10 then deenergizes the bladder 34b and closes clamps 36 and 38.

The operator then places the cuff 64 on the arm of the donor D and inflates it. The operator then pierces a vein in the arm of the donor D with the sterile cannula 70. This step places the set 14 in a bi-directional fluid flow communication with the donor. This communication is continuously maintained through the following draw and return cycles. The operator then depresses the START button 66d to initiate the first draw and return cycle.

The first draw-return cycle is then commenced and clamps 36, 38, 60, 62 and 93 are opened. Blood, mixed with anticoagulant, flows under the influence of gravity into the container 86. The unit 24 can be set for a 7 minute draw cycle. When bag 86 contains 500 ml of whole blood, the housing 34 will prevent additional inflow and no further blood will be given up by the donor.

Part way through the seven minute draw cycle, clamp 62 is deenergized by the unit 24. The flow of anticoagulant is then decreased during the completion of the draw cycle.

At the end of the seven minute draw cycle, clamps 60 and 38 are deenergized by the unit 24 along with the cuff 64. The bladder 34b is energized by the unit 24. Whole blood is forced through the separator 90. Plasma is collected in the container 94 and simultaneously the concentrated red blood cells are returned to the donor D via the bi-directional fluid flow conduit 72, 78 and the single lumen cannula 70. When the system 10 has completed the return cycle, the clamp 36 is deenergized. The system 10 waits until the operator again presses the START button 66d. Once the START button 66d has been depressed, the unit 24 reinflates the cuff 64 and initiates the next draw cycle.

After the third draw-return cycle the container 94 will contain 500 ml of plasma. Housing 50 limits the separated plasma to only 500 ml. In the event the container 94 becomes filled with plasma prior to the end of the third draw cycle, the housing 50 will block further inflow of plasma. The remainder of the whole blood will then be returned to the donor D. The cannula 70 is removed from the arm of the donor D. The operator again depresses the LOAD button 66a. All of the clamps are then energized by the unit 24. The set 14 can then be removed. The plasma container 94 can be removed from the set 14 and sealed as is conventional. The remainder of the set can then be thrown away. The system 10 is then ready for the next donor.

As before stated, the force application system 34b can take the form of a variety of devices to produce the necessary expressing forces. For example, a standard spring actuated plasma expressor of a type marketed by the Fenwal Division of Travenol Laboratories, Inc., Model No. 4R4414, could be used to apply force to the collection bag 86 thereby forcing the whole blood through the separator 90. It has been found, however, that such a device exerts a force which expresses the whole blood from the container 86 with an output pressure that varies substantially with time as the container 86 is being emptied.

Preferably the separator 90 will be a hollow membrane fiber filter. It would be desirable from the point of view of optimizing the design of the filter 90 to be able to express the whole blood from the container 86 at a substantially constant, predetermined, pressure.

For purposes of the present disclosure, the phrase "substantially constant predetermined pressure" shall mean a selected, applied pressure that remains essentially constant during the time period during which the whole blood is being forced from the container 86. A pressure variation of 10 or 20% during the first 80 to 90% of the time during which the container 86 is being emptied would still come within the present definition of a substantially constant pressure system.

The system 10 is thus a constant pressure system as opposed to a constant volume system, in which a relatively constant volume of fluid is pumped through the system per unit of time. The system 10, as a constant pressure system, has the further advantage that if a line such as 84a, 85 or 78 becomes crimped or blocked during the return portion of a draw-return cycle, the pressure present therein will not increase as might be the case in a constant volume system.

Figure 7A:
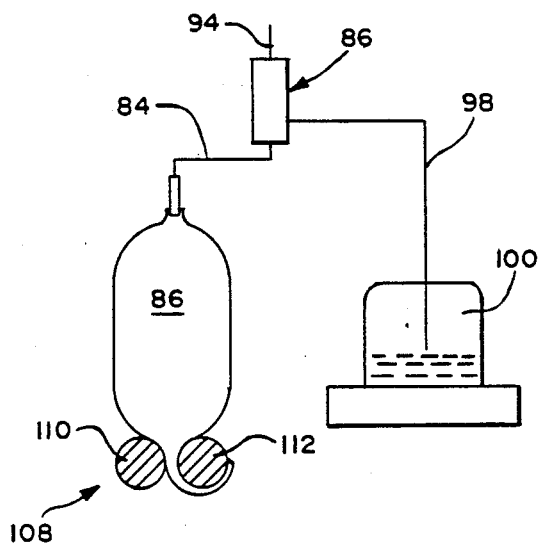
FIG. 7A is a side, schematic view of an apparatus for forcing whole blood out of the collection container.
Figure 7B:
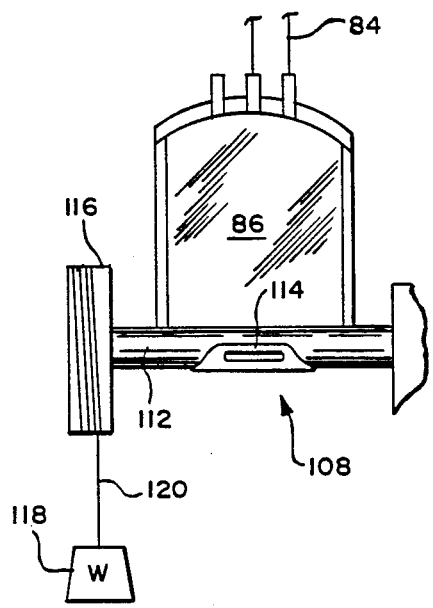
FIG. 7B is a front, schematic view of the apparatus of FIG. 7A.

A system 108 which will express the whole blood from the container 86 into the separator 90 at a substantially constant predetermined pressure is illustrated in FIGS. 7A and 7B. This system 108 includes means for holding the variable volume container 86, which includes an element 111 rotatably supported adjacent to the container 86. As shown in FIG. 7B, means 113 is provided for pressing the element 111 against the container 86 to reduce its volume while rotating the element 111 to sequentially advance the container 86 by the element 111.

As a result, the fluid accumulated in the container 86 (which, in the illustrated embodiment, is whole blood) is expressed into the separator 90. In accordance with the invention, the rotation means 113 applies a substantially constant torque to the element 111 so that fluid is expressed at a substantially constant pressure.

The element 111 can be variably constructed. In the embodiment illustrated in FIGS. 7A and 7B, the element 111 includes a pair of spaced apart rollers 110 and 112.

The rollers 110 and 112 are oriented so as to be parallel with a space therebetween. For example, the rollers might have a diameter on the order of ¾ of an inch and have an inter-roller gap of one-eighth of an inch. As illustrated in FIGS. 7A and 7B, the container 86 is positioned with a lower tab located in a slot 114 in the roller 112 to hold the container 86 in an operative relationship with the rollers 110 and 112.

In this embodiment, the rotation means 113 comprises a self-contained energy source for the rollers 110, 112, including means for releasably storing a quantity of energy to rotate the rollers 110, 112, as well as means for selectively introducing energy into the energy storage means.

While the above-described energy storage and introduction means can be variously constructed, as shown in FIG. 7B, they take the form of a pulley 116 attached to an end of the roller 112. A weight 118 is attached via a flexible cable or line 120 to the pulley 116. By recoiling or rewinding the line 120 upon the pulley 116 after each use, the pulley 116 can be, in effect, "recharged" for subsequent use.

Experiments have indicated, that notwithstanding the fact that the blood container 86 is flexible and of irregular geometry, as the weight 118 unwinds, due to the force of gravity, the force generating apparatus 108 applies a constant torque to the rollers 110 and 112 to compress the container 86 while at the same time advancing the container 86 past the rollers 110, 112. As a result, the whole blood is expressed into the separator 90 at a substantially, constant pressure.

As the blood is sequentially forced from the bag 86, the empty portion of the bag 86 is wrapped around the roller 112. As the weight 118 continues to descend from the pulley 116, the bag 86 is continually drawn between the two rollers 110 and 112 and wrapped around the roller 112.

The system 108 will express the whole blood to the filter 90 at a substantially constant pressure on the order of 160 to 180 millimeters of mercury.

Figure 8:
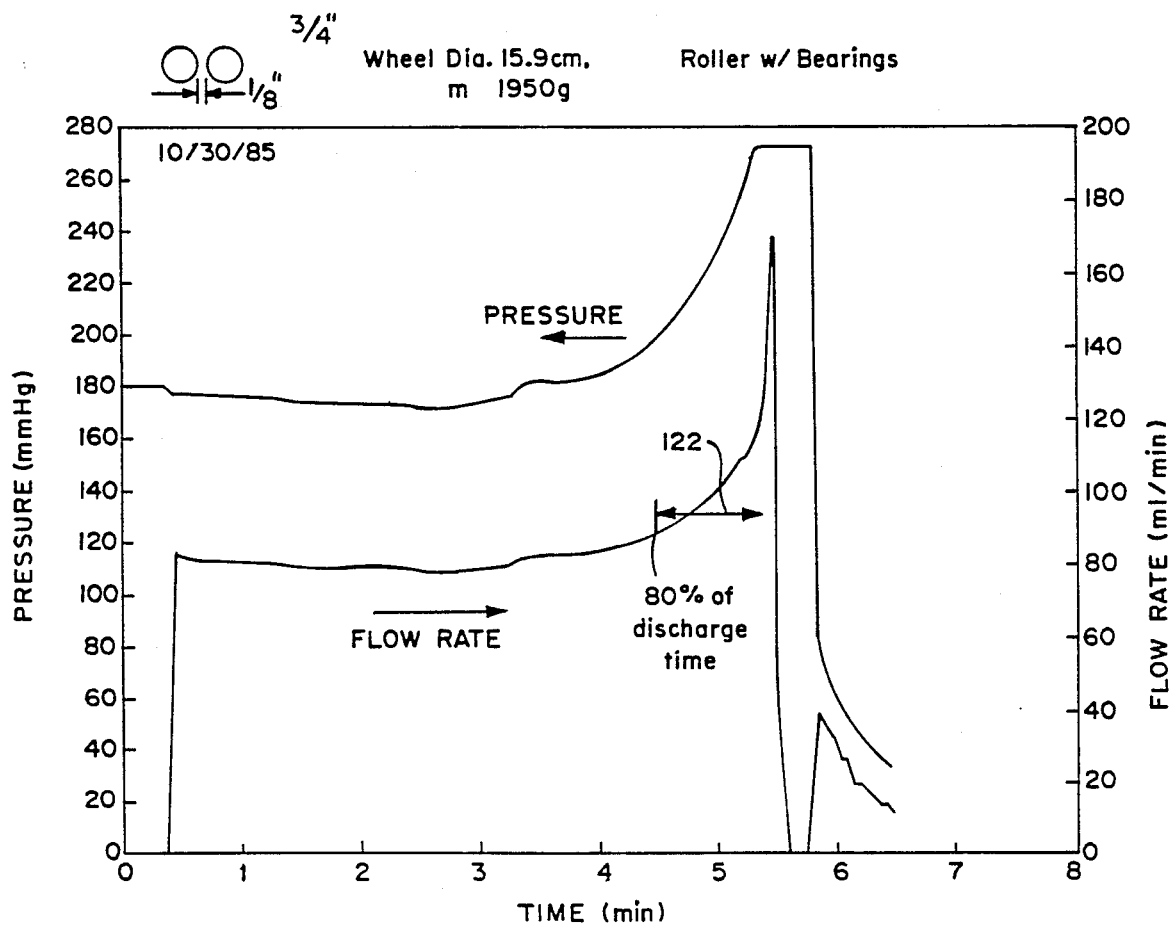
FIG. 8 is a graph of pressure versus time generated by the apparatus of FIGS. 7A and 7B along with a graph of flow rate versus time.

FIG. 8 is a plot of pressure versus time as the weight 118 rotates the roller 112. Flow rate versus time is plotted on the same graph. Fluid pressure is substantially constant at 180 mm of mercury for the initial 80 percent of discharge time. The last 20 percent, region 122, displays an increase in pressure and related increase in flow rate. These increases appear to be related to a rapid decrease in contact area between bag 86 and rollers 110, 112 as the bag is emptied. The presence of this spike does not preclude the roller system 108 from being a generator of substantially constant pressure as that phrase has been defined and used herein.

To generate pressures in a range of 160–180 mm of mercury, a weight 118 with a mass of 1950 g was used. The pulley 116 had a diameter of 15.9 cm. Larger or smaller pressures can be generated by varying the mass of the weight 118.

Figure 9:
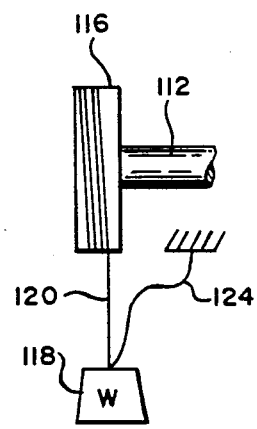
FIG. 9 is an enlarged, schematic view of a portion of the apparatus of FIGS. 7A and 7B modified so as to improve the substantially, constant pressure characteristics thereof as the blood collection bag empties.

The effects of the spike can be attenuated by means of a stretchable or elastic, silicone tubing member attached to the weight 118 to slow its rate of descent during the last 20 percent of the discharge time, as shown in FIG. 9. There one end of a stretchable WACO 78170-10 silicone tubing member 124 was affixed to the weight 118. The other end of the member 124 was affixed to a stationary region or support for the roller 112.

Figure 10:
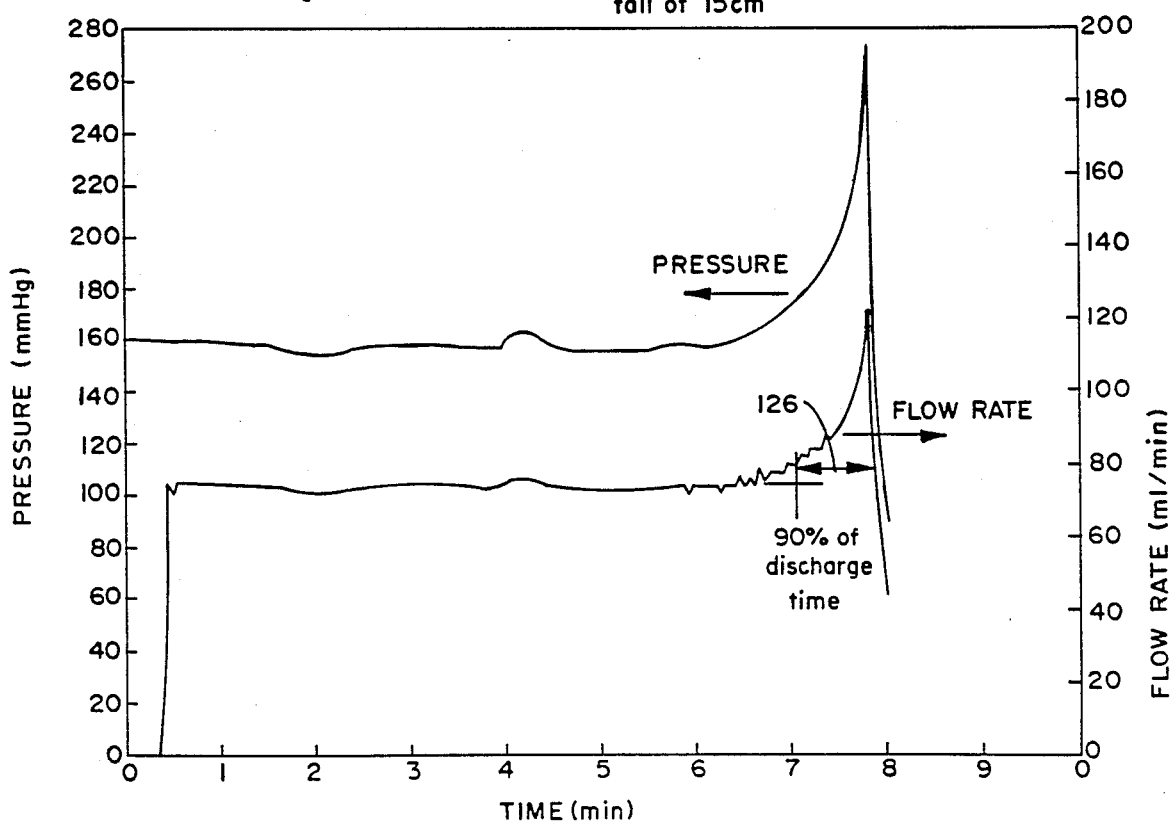
FIG. 10 is a graph of pressure versus time along with flow rate versus time as a result of using the modified apparatus of FIG. 9.

As illustrated in FIG. 10, the time interval of substantially constant fluid pressure was, as a result, expanded from 80% to 90% of the discharge period. In this instance, a weight 118 with a mass of 4.81 kg was used in combination with a pulley 116 having a diameter of 5.71 cm.

FIG. 10 is a plot of fluid pressure versus time and flowrate versus time as a result of using the modified system of FIG. 9. As illustrated in FIG. 10, increases in fluid pressure and flow rate appear in a region 126. Region 126 is initiated at approximately 90 percent of the discharge time. Thus, the elastic tubing member 124, by showing the rate of descent of the weight 118 during the end portion of its descent period, is effective to extend the substantially constant pressure though about 90 percent of the discharge period. As compared to the spikes of pressure and flow rate in the region 122 of FIG. 8, the spikes of pressure and flow rate in the region 126 of FIG. 10 are substantially attenuated.

Figure 11:
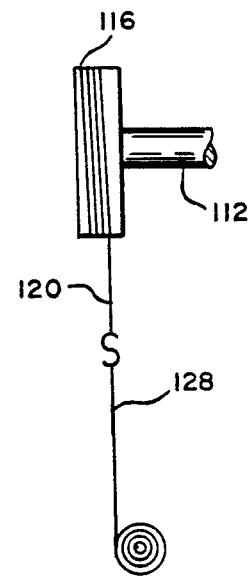
FIG. 11 is an enlarged, schematic view of a portion of the apparatus of FIGS. 7A and 7B modified so as to use a constant force spring instead of a hanging weight.

Alternately, as illustrated in FIG. 11, instead of using the weight 118 as the energy source, a conventional spring 128 which exerts a constant force as it is being extended or as it is being retracted can be used to rotate the pulley 112. Such a spring 128, with a seven pound force has been used. It has been found experimentally that in connection with the system 108 the use of the constant-force seven pound spring to apply an essentially constant torque to the rollers 110, 112 results in an output pressure on the order of 140 millimeters of mercury.

In this embodiment, the spring 128 serves as the energy storage device which can be selectively recoiled or extended, as appropriate after use, and thereby "recharged" by the operator for subsequent use.

Figure 12:
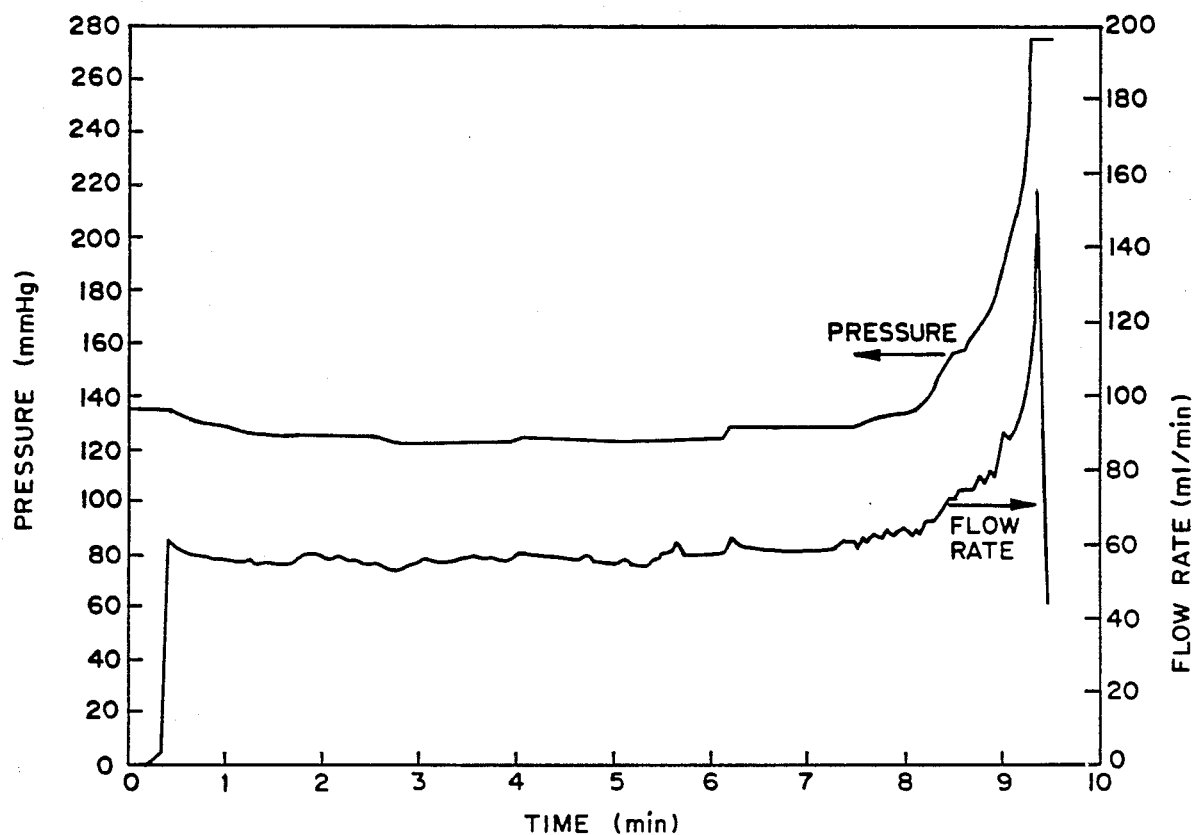
FIG. 12 is a graph of pressure versus time, along with flow rate versus time, as a result of using the apparatus of FIG. 11.

FIG. 12 is a plot of fluid pressure versus time and flow rate versus time as a result of using the constant-pressure spring 128 of FIG. 11.

Figure 11A:
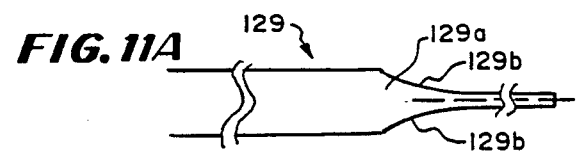
FIG. 11a is an enlarged planar view of a portion of a substantially constant force spring with a continuously tapered end region.

The increase in output pressure near the end of the return time period, as illustrated in FIG. 12, can be substantially eliminated by using a spring, such as the spring 129 in FIG. 11a, which has a tapered end region. The spring 129 is a substantially constant force spring with a variable force, tapered end region 129a. The tapered end region 129a will apply a force to the blood container as the spring is unrolled, near the end of the return period, which has a magnitude less than the magnitude generated by the remaining portion of the spring 129. As illustrated in FIG. 11a, the edges 129b of the end region 129a can be continuously varied in accordance with a predetermined function along the length of the end region 129a.

For example, edges 129b can be formed such that there is a hyperbolic reduction in the cross-sectional area of the spring end region 129a as a function of the distance along the end region. This corresponds generally to the shape of the increased pressure near the end of the return cycle in FIG. 12. Depending on the characteristics of the collection container 86, alternate functions can be used to modify the cross-sectional area of the end region 129a as that spring is unrolled. For example, linear or parabolic changes in cross sectional area as a functin of distance along the spring end region could also be used. These alternate end region geometries can be used to compensate for increases in pressure that differ, as a function of time, from the pressure increase illustrated in FIG. 12.

As an alternate to the roller system 108, and as earlier shown in the system 10 shown in FIG. 5, a commercially available inflatable bladder in a rigid container may be used. In this instance, the housing 34 of FIG. 1 corresponds to an external housing of the bladder 34b.

Figure 13:
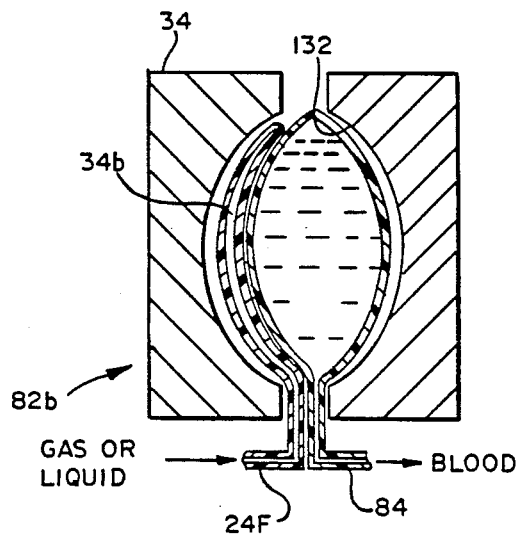
FIG. 13 is a side, schematic view of a preferred apparatus for forcing whole blood out of the collection container.

FIG. 13C illustrates a system utilizing such a force generating system. An external metal or rigid plastic housing 34 has a cavity 132 defined therein. The inflatable bladder 34b is positioned in the cavity 132. The blood collection bag 86 is placed in the cavity 132. Tubing 24f is provided to inflate the bladder 34b.

The bladder 34b is located adjacent the blood bag 86 and can be inflated by means of pressure from a gas or a liquid. For example, a regulated gas could be used, a liquid $CO_2$ cartridge could be used, or a gas or liquid under pressure due to a piston could also be used.

As the source of energy inflates the bladder 34b in the housing 34, the blood in the bag 86 is expressed into the tubing 84 at a substantially constant pressure. This pressure can be adjusted to be in a range of 160 to 180 millimeters of mercury as in the case with the dual roller system 108. The pressure should be adjusted in accordance with the resistance of the filter 90 and related flow circuits to provide physiologically acceptable return flow rates in a range of 40 to 80 cc per minute.

Figure 14:
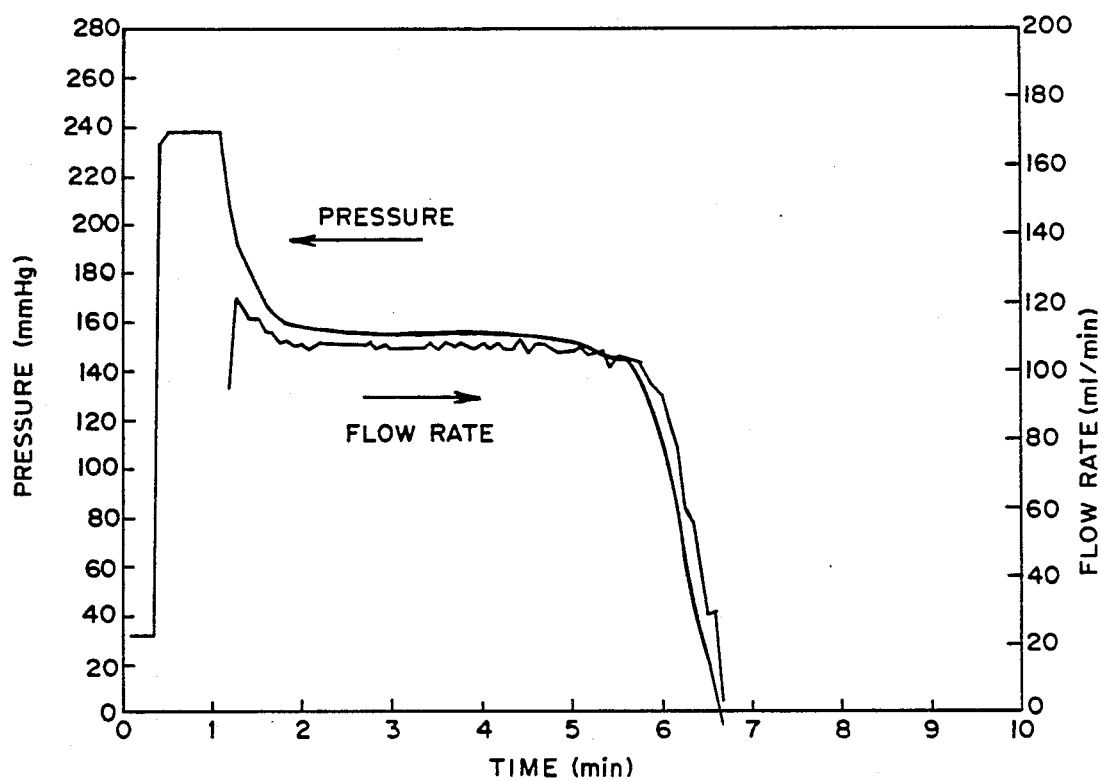
FIG. 14 is a graph of pressure versus time, along with flow rate versus time, as a result of using the apparatus of FIG. 13.

FIG. 14 is a plot of fluid pressure versus time and flow rate versus time where a bladder system 82b is energized by a standard $CO_2$ cartridge. It has been found experimentally that a single 12 g $CO_2$ cartridge will inflate the bladder 134 to produce a substantially constant 160 mm of mercury pressure as illustrated in FIG. 10, 4-6 times. Hence, one $CO_2$ cartridge can provide adequate energy for several pheresis cycles with a single donor.

Using the bladder system, the size of the cavity 132 and bladder 34b limit the volume of blood that can accumulate in the container 86. Hence, after 500 ml. have been accumulated in the container 86, the flow of whole blood essentially ceases. Similarly, housing 50 can be used to limit the volume of plasma that accumulates in the container 94.

The bladder system of FIG. 13C does not generate a spike of increased pressure and flow rate at the end of the return period. Instead, as illustrated in FIG. 14, as the container 86 is emptied at the end of the return cycle, the generated pressure and flow rates decrease.

Figure 15:
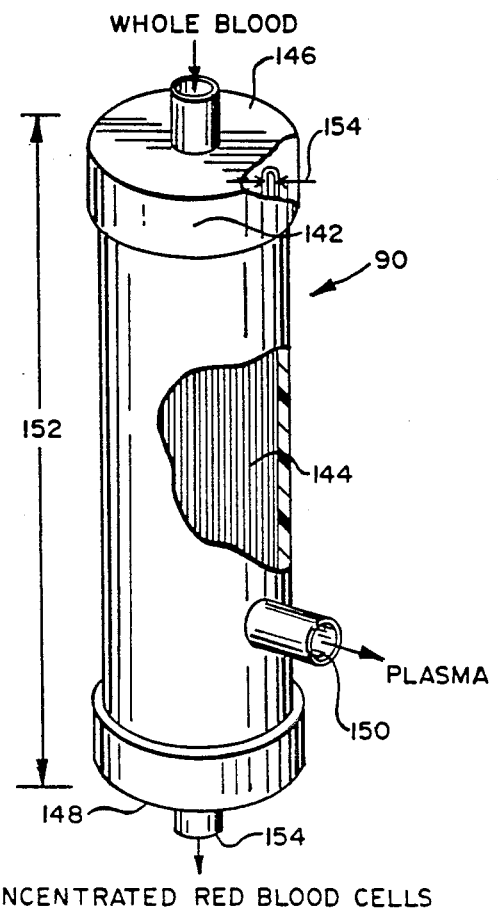
FIG. 15 is a fragmentary side view, partly in section, of a filter usable with the system of the present invention.

FIG. 15 illustrates an exemplary membrane filter usable with the system 10. The filter 90 includes a hollow cylindrical housing 142 in which is positioned a plurality of hollow fiber membranes 144. The housing 142 includes a blood inlet port 146, an outlet port 148 and a plasma output port 150. Fluid flow from the outlet port 148 is composed of concentrated red blood cells. This fluid can be regarded as a residual blood component.

The hollow fiber membranes, such as membranes 144, are suitable for contact with human blood and can be formed of polypropylene, polyethylene-co-vinyl alcohol, nylon polysulfone or other materials. The fiber members 144 are oriented axially within the housing 142 such that the whole blood flows therethrough from end to end of the filter. The membranes are microporus and contain pores with diameters in a range of 0.1 to 5 microns preferably in a range of 0.2 to 0.6 microns.

One consideration in the design of filters such as the filter 90 is minimization of the risk of hemolysis. For given input pressures in a range of 160 to 180 millimeters of mercury, filter parameters of Table I define membrane filters with minimal risk of hemolysis for a given cost.

Each of the six filters defined by Table I includes hollow filtration fibers with each file having a length (L) 152 and an internal diameter (D) 154. The number of fibers (N) defines the number to be axially located in a give housing.

TABLE I

| P (mmHg) | N | L (cm) | D (m) |
|---|---|---|---|
| 100 | 3099 | 7.00 | 192 |
| 150 | 2209 | 7.00 | 189 |
| 100 | 2492 | 7.00 | 202 |
| 150 | 1731 | 7.00 | 198 |
| 100 | 1889 | 7.00 | 213 |
| 150 | 1347 | 7.00 | 209 |

Use of a filter with one set of the above parameters will result in extraction of 40 to 70% of the plasma in the whole blood which passes through the filter. Table I also illustrates in each instance the optimized parameters of a hollow membrane filter used in a system with a predetermined pressure drop (P) between the inlet port 146 and the outlet port 148 of each filter design. As can be seen, the number of fiber members decreases as the pressure drop across the filter is increased. Care must always be taken to insure that the force generating system provides enough pressure at the outlet port 148 to return the filtered blood to the donor D. Thus, for a predetermined pressure drop across the filter, it is possible to optimize the design of the filter. Operating the filter at the predetermined pressure drop optimizes collection of the separated blood component.

The present method and apparatus are particularly advantageous in that, given a substantially constant input pressure, the design and characteristics of the hollow fiber filter 90 can be optimized to provide efficient separation of the plasma component from the whole blood with minimal danger of hemolysis. In addition, the system 10 uses the disposable set 14 that is relatively inexpensive. The system 10 is easy to use and is portable to church basements or recreation halls where blood collection centers are often temporarily established.

The present method and apparatus have been disclosed in exemplary terms of separating and collecting plasma. The present invention, it will be understood, is not limited to plasma collection and separation. The separation and collection of a selected blood component, other than plasma, in accordance with the present apparatus and method are within the spirit and scope of the present invention. For example, leukocytes, lipids, lymphocytes, T-cell subsets, lipoprotein, other lipid moieties, auto-antibodies, immune complexes or the like could be separated and collected in accordance with the present method and apparatus.

It will also be understood that the present apparatus for generating substantially constant pressure can be used in connection with the delivery of alternate solutions from flexible containers. The types of solutions can include parenteral, medicinal, or nutritional solutions which need to be delivered at a substantially constant pressure.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. It is, of course, intended to cover by the appended claims all such modifications as fall within the scope of the claims.

What is claimed is:

1. A fluid separation system comprising
a variable volume container for accumulating a desired volume of fluid,
means for separating the fluid into component parts,
means for holding said variable volume container, including an element rotatably supported adjacent to said variable volume container, and
means including a mass subject to the force of gravity for generating an essentially constant torque to press said element against said variable volume container to reduce its volume while rotating said element to advance said container by said element and sequentially express the accumulated fluid from said container into said separation means at a substantially constant pressure, said mass being coupled to said rotatably mounted element by an elastic tubing member to slow the rate of descent of said mass.

2. A system according to claim 1
wherein said rotating element includes first and second spaced-apart rotating members between which said variable volume container is compressed while being advanced in response to the rotation of said first and second rotating members.

3. A blood component system comprising
a variable volume container,
means for accumulating a desired volume of whole blood from a donor in said variable volume container,
means for separating whole blood into component parts,
means for holding said variable volume container including an element rotatably supported adjacent to said variable volume container, and
means including a mass subject to the force of gravity for generating an essentially constant torque to press said element against said variable volume container to reduce its volume while rotating said element to advance said container by said element and sequentially express the whole blood from said container into said separation means at a substantially constant pressure, said mass being coupled to said rotatably mounted element by an elastic tubing member to slow the rate of descent of said means.

4. A blood component system comprising
a variable volume container,
means for accumulating a desired volume of whole blood from a donor in said variable volume container,
means for separating whole blood into component parts,
means for holding said variable volume container including an element rotatably supported adjacent to said variable volume container,
means for pressing said element against said variable volume container to reduce its volume while rotating said element to advance said container by said element and sequentially express the whole blood from said container into said separation means, and
means for collecting at least one of the component parts from said separation means while returning at least one of the component parts to the donor in response only to the force applied by said pressing and rotating means.

5. A blood component separation system according to claim 4;
wherein said pressing and rotating means includes means for expressing the whole blood from said container into said separation means at a substantially constant pressure.

6. A blood separation system according to claim 5;
wherein said pressure and rotating means includes means for generating an essentially constant torque to express the whole blood from said container into said separation means at a substantially constant pressure.

7. A blood component separation system according to claim 4 or 5;
wherein said separation means includes a filter.

8. A blood component separation system according to claim 4
wherein said rotating element includes first and second spaced-apart rollers between which said variable volume container is compressed while being advanced in response to the rotation of said rollers.

9. A blood component separation system according to claim 8
wherein said pressing and rotating means includes means for generating an essentially constant torque to said rollers to express the whole blood at a substantially constant pressure.

10. A blood component separation system according to claim 9
wherein said separation means includes a filter.

11. A fluid separation system comprising
a variable volume container for accumulating a desired volume of fluid,
means for separating the fluid into component parts,
means for holding said variable volume container, including an element rotatably supported adjacent to said variable volume container, and
spring means for pressing said element against said variable volume container to reduce its volume while rotating said element to advance said container by said element and sequentially express the accumulated fluid from said container into said separation means, said spring means including a first region for applying a first force to express fluid from said container at a first pressure, and a second region for applying a second force having a magnitude different than said first force to express fluid from said container at a pressure different than said first pressure.

12. A system according to claim 11
wherein said rotating element includes first and second spaced-apart rotating members between which said variable volume container is compressed while being advanced in response to the rotation of said first and second rotating members.

13. A blood component system comprising
a variable volume container,
means for accumulating a desired volume of whole blood from a donor in said variable volume container,
means for separating whole blood into component parts,
means for holding said variable volume container including an element rotatably supported adjacent to said variable volume container, and
spring means for pressing said element against said variable volume container to reduce its volume while rotating said element to advance said container by said element and sequentially express the whole blood from said container into said separation means, said spring means including a first region for applying a first force to express whole blood from said container at a first pressure and a second region for applying a second force having a magnitude different than said first force to express whole blood from said container at a pressure different than said first pressure.

14. A system for forcing fluid from a variable volume container at a substantially constant pressure comprising,
means for holding said variable volume container including an element rotatably supported adjacent to said variable volume container, and
means including a mass subjected to the force of gravity for pressing said element against the variable volume container to reduce its volume while generating an essentially constant torque to rotate said element to advance the container by said element and sequentially express fluid from the container at a substantially constant pressure, said mass being coupled to said rotatably mounted element by an elastic tubing member to slow the rate of descent of said mass.

15. A system according to claim 14
wherein said rotating element includes first and second spaced-apart rotating members between which said variable volume container is compressed while being advanced in response to the rotation of said first and second rotative members.

16. A blood component system comprising
a variable volume container,
means for accumulating a desired volume of whole blood from a donor in said variable volume container,
means for separating whole blood into component parts,
conduit means for conveying the whole blood from said variable volume container to said separation means,
means for holding said variable volume container including an element rotatably supported adjacent to said variable volume container, and
means for pressing said element against said variable volume container to reduce its volume while rotating said element to advance said container by said element and sequentially express the whole blood from said container through said conduit means into said separation means, said pressure and rotating means includes means for generating an essentially constant torque to express the whole blood from said container into said separation means at a pressure which remains substantially constant despite variations in fluid resistance occurring in said conduit means.

17. A blood component separation system according to claim 16
wherein said rotating element includes first and second spaced-apart rollers between which said variable volume container is compressed while being advanced in response to the rotation of said rollers.

18. A blood component separation system according to claim 16
wherein said separation means includes a filter.

19. A blood component separation system according to claim 16
wherein said rotating element includes first and second spaced-apart rollers between which said variable volume container is compressed while being advanced in response to the rotation of said rollers.

20. A blood component separation system according to claim 19
wherein said separation means includes a filter.

21. A system for forcing fluid from a variable volume container at a substantially constant pressure comprising,
means for holding said variable volume container including an element rotatably supported adjacent to said variable volume container, and
spring means for pressing said element against the variable volume container to reduce its volume while generating torque to rotate said element to advance the container by said element and sequentially express fluid from the container, said spring means including a first region for generating a first essentially constant torque to rotate said element and express fluid from the container at a first substantially constant pressure and a second region for generating a second torque different than the first torque to rotate said element and express fluid from the container at a second pressure different than the first pressure.

22. A system according to claim 21
wherein said rotating element includes first and second spaced-apart rotating members between which said variable volume container is compressed while being advanced in response to the rotation of said first and second rotative members.

* * * * *